United States Patent
Bourne et al.

(10) Patent No.: US 11,433,155 B2
(45) Date of Patent: Sep. 6, 2022

(54) WICK-BASED VOLATILE SUBSTANCE DIFFUSER

(71) Applicant: Energizer Brands II, LLC, St. Louis, MO (US)

(72) Inventors: Christopher Bourne, Painesville, OH (US); Matthew R. Gallen, Parma, OH (US)

(73) Assignee: Energizer Group Limited, High Wycombe (GB)

( * ) Notice: Subject to any disclaimer, the term of this patent is extended or adjusted under 35 U.S.C. 154(b) by 233 days.

(21) Appl. No.: 16/246,279

(22) Filed: Jan. 11, 2019

(65) Prior Publication Data

US 2020/0222572 A1    Jul. 16, 2020

(51) Int. Cl.
*A61L 9/12*    (2006.01)

(52) U.S. Cl.
CPC ................................. *A61L 9/127* (2013.01)

(58) Field of Classification Search
CPC .................................. A61L 9/127; A61L 9/12
See application file for complete search history.

(56) References Cited

U.S. PATENT DOCUMENTS

| | | | |
|---|---|---|---|
| 4,621,768 A | 11/1986 | Lhoste et al. | |
| 4,840,773 A * | 6/1989 | Wade | B60H 3/0007 239/43 |
| 7,243,859 B2 * | 7/2007 | Caserta | A61L 9/127 239/34 |
| 7,854,393 B2 * | 12/2010 | DiBello | A61L 9/037 239/34 |
| 2005/0001053 A1 | 1/2005 | Zobele | |
| 2007/0119963 A1 | 5/2007 | Dibello et al. | |

FOREIGN PATENT DOCUMENTS

| | | |
|---|---|---|
| EP | 2047868 A2 | 4/2009 |
| ES | 1062190 U | 6/2006 |
| FR | 2695305 A1 | 3/1994 |

OTHER PUBLICATIONS

PCT International Search Report and Written Opinion from the International Search Authority regarding PCT/US2020/12830 dated May 4, 2020; 16 pp.

* cited by examiner

*Primary Examiner* — Steven M Cernoch
(74) *Attorney, Agent, or Firm* — Lee & Hayes, P.C.

(57) ABSTRACT

A wick-based diffuser is configured for diffusing a liquid volatile substance composition into an air flow path extending through the diffuser to disseminate the volatile substance composition throughout a surrounding volume (e.g., a vehicle interior). Diffusers may comprise a body defining a hollow interior and having an air flow path extending therethough; a reservoir; a wick extending from the reservoir and into the hollow interior of the body; and a closure mechanism configured to selectably isolate the wick and the reservoir from the air flow path extending through the body. Wick-based diffusers may be mounted to a support device via a low-friction mounting mechanism located above a center of gravity of the diffuser, such that the diffuser self-aligns in an upright orientation under the influence of gravity.

19 Claims, 7 Drawing Sheets

WICK-BASED VOLATILE SUBSTANCE DIFFUSER

FIELD

Various embodiments relate generally to volatile substance diffusers, such as air fresheners.

BACKGROUND

Different types of volatile substance diffusers have been developed, particularly air fresheners for use in vehicles. Due to continually changing customer preferences, new diffuser configurations are constantly needed.

BRIEF SUMMARY

Various embodiments are directed to a self-leveling (also-referred to as self-righting) diffuser (e.g., air freshener) configured for dispersing a volatile substance (e.g., a fragrance) adjacent an external air circulator (such as an air vent of a vehicle). The diffuser is rotatably secured relative to a mounting mechanism (e.g., a vent clip) via a low friction joint, such as a low friction ball joint. The low-friction joint is located above a center of gravity of the diffuser (particularly when a substance reservoir located within a second body portion of the diffuser is at least partially filled with a liquid substance, such as a fragrance), such that the diffuser will rotate about the low friction joint under the influence of gravity to self-align in an upright configuration.

Moreover, diffusers according to various embodiments are wick-based air fresheners defined by a wick partially submerged within a volatile substance liquid and configured to draw the volatile substance liquid upward via a capillary action into an exposed portion of the wick located within an air circulation region of the air freshener. The volatile substance liquid drawn into an exposed portion of the wick located within the air circulation region evaporates and is circulated out of the diffuser and into a surrounding environment. The diffuser additionally comprises a closure mechanism configured to selectably isolate the wick and reservoir from an air flow path extending through the diffuser to prevent unintentional leakage of the volatile substance liquid from the reservoir when the diffuser is inverted. The closure mechanism comprises a wick cap and corresponding gasket located movable vertically within the interior of the diffuser via a cam mechanism configured for translating rotational movement of a second body portion of the diffuser into vertical movement of the wick cap. The wick cap moves vertically along the exposed portion of the wick between a sealed configuration, in which the exposed portion of the wick is housed within the wick cap and the gasket is depressed between the wick cap and a gasket seat, such that the gasket is sealed against a gasket seat surrounding a wick aperture leading into the reservoir, and an exposed configuration, in which the exposed portion of the wick is accessible to air circulating through the air freshener and the wick cap and gasket are spaced away from the gasket seat. When in the sealed configuration, the gasket prevents volatile substance liquid from leaking through the wick aperture, even when the diffuser is inverted.

Various embodiments are directed to a diffuser. The diffuser comprising: a body defining a hollow interior and having an air flow path extending therethough; a wick configured for holding a volatile substance composition therein and positioned at least partially within the hollow interior of the body; and a closure mechanism configured to selectably isolate the wick from the air flow path extending through the body.

In certain embodiments, the diffuser comprises a reservoir, and wherein: the wick extends from the reservoir and into the hollow interior of the body; and the closure mechanism is configured to selectably isolate the wick and the reservoir from the air flow path extending through the body. In certain embodiments, wherein the closure mechanism comprises a wick cap movable linearly between: a sealed configuration in which the wick and the volatile substance composition are isolated from the air flow path; and an exposed configuration in which at least a portion of the wick positioned within the hollow interior of the body is exposed to the air flow path. In certain embodiments, wherein the reservoir defines a wick aperture extending therethrough and the wick aperture is surrounded by a gasket seat, and wherein, in the sealed configuration, the wick cap depresses a gasket against the gasket seat.

Moreover, in certain embodiments, the body is a first body portion; the reservoir is defined within a second body portion rotationally secured relative to the first body portion; and the closure mechanism additionally comprises a cam mechanism configured to convert rotational movement of the second body portion relative to the first body portion into linear movement of the wick cap between the sealed configuration and the exposed configuration. In various embodiments, the cam mechanism is defined by: one or more splined cam slots within a sidewall of the second body portion; and one or more cam pins each extending laterally away from an exterior surface of the wick cap and into one of the one or more splined cam slots. Moreover, the cam mechanism may be further defined by one or more vertical travel slots extending through a sidewall of a third body portion positioned within the hollow interior of the first body portion and rotationally immobile relative to the first body portion, wherein each of the one or more cam pins extends through one of the one or more vertical travel slots. In certain embodiments, the cam mechanism defines one or more lockout positions to selectably lock the cam pin in: a first vertical position corresponding to the sealed configuration; or a second vertical position corresponding to the exposed position. Moreover, in various embodiments the cam pin is configured to frictionally engage edges of the cam slots such that the wick cap is infinitely adjustable between the sealed configuration and the exposed configuration.

In certain embodiments, the body is a first body portion; the reservoir is defined within a second body portion rotationally secured relative to the first body portion; and the closure mechanism is configured to selectably isolate the wick and the reservoir from the air flow path extending through the first body portion based on the rotational position of the second body portion relative to the first body portion. Moreover, in certain embodiments the diffuser comprises a low friction mounting mechanism for securing the diffuser relative to a support device, wherein the low friction mounting mechanism is secured relative to the body at a location above a center of gravity of the diffuser.

Various embodiments are directed to a diffuser comprising: a body comprising a reservoir of a fragrance composition and a wick for diffusing the fragrance composition therefrom, the body having an upright orientation wherein the reservoir is positioned below the wick; and a self-righting mounting mechanism coupled to the body, the self-righting mechanism configured to allow the reservoir to rotate the body to the upright position from a non-upright position.

In certain embodiments, the body comprises a reservoir configured for supporting the volatile substance composition therein, and wherein the reservoir is located below a center of gravity of the diffuser. Moreover, the reservoir may be at least partially transparent to enable a user to view a quantity of fragrance composition therein. In certain embodiments, the diffusing mechanism comprises a wick extending from the reservoir to an exposed portion of the wick positioned within the air flow path. Moreover, the diffuser may further comprise a closure mechanism configured to selectably isolate the wick and the reservoir from the air flow path extending through the portion of the body.

In certain embodiments, the wick extends through a reservoir upper wall between an interior of the reservoir of fragrance composition and an air flow path extending through a portion of the body. Moreover, the diffuser may further comprise a closure mechanism configured to selectively isolate the wick and the reservoir from the air flow path extending through the body. In certain embodiments, the self-righting mounting mechanism comprises a low friction mounting mechanism for securing the diffuser relative to a support device. In various embodiments, the low friction mounting mechanism is secured relative to a body at a location above a center of gravity of the diffuser. Moreover, the low friction mounting mechanism may comprise a ball-and-socket joint.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Figure 1:
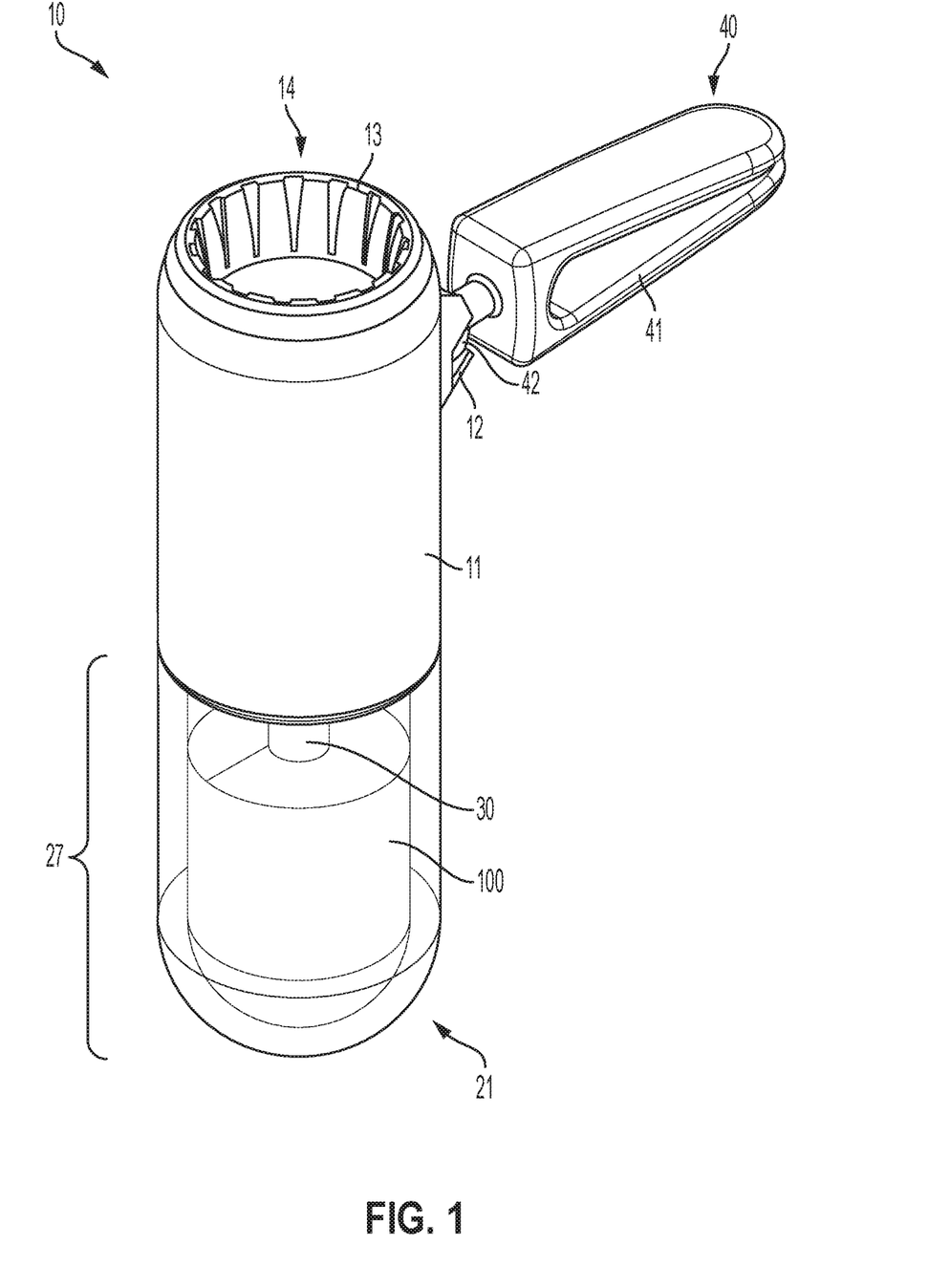
FIG. 1 shows a perspective view of a diffuser according to one embodiment.

FIG. 1 shows a diffuser 10 according to one embodiment. The various components of the diffuser 10 may comprise one or more plastic materials, one or more metal materials, one or more paper materials, one or more wood materials, one or more fragrant polymers, and/or various combinations thereof. The illustrated diffuser 10 may be configured for circulating a volatile substance composition 100 stored within a reservoir by drawing the volatile substance composition 100 up a wick and evaporating the volatile substance composition 100 from an exposed wick portion into an air stream circulating through the diffuser 10.

It should be understood that any of a variety of volatile substance compositions 100 may be utilized with the diffuser 10. For example, fragrance compositions (fragrant organic compounds, fragrant volatile oils, fragrant synthetic compounds, and/or the like), deodorizers, disinfectant compositions, medicinal compositions, aroma therapy compositions, insecticides, and/or the like may be dispersed via the diffuser 10. In certain embodiments, the diffuser 10 may be embodied as a fragrance diffuser (also known as an air freshener), however other configurations may be possible in accordance with various embodiments discussed herein.

Figure 2A:
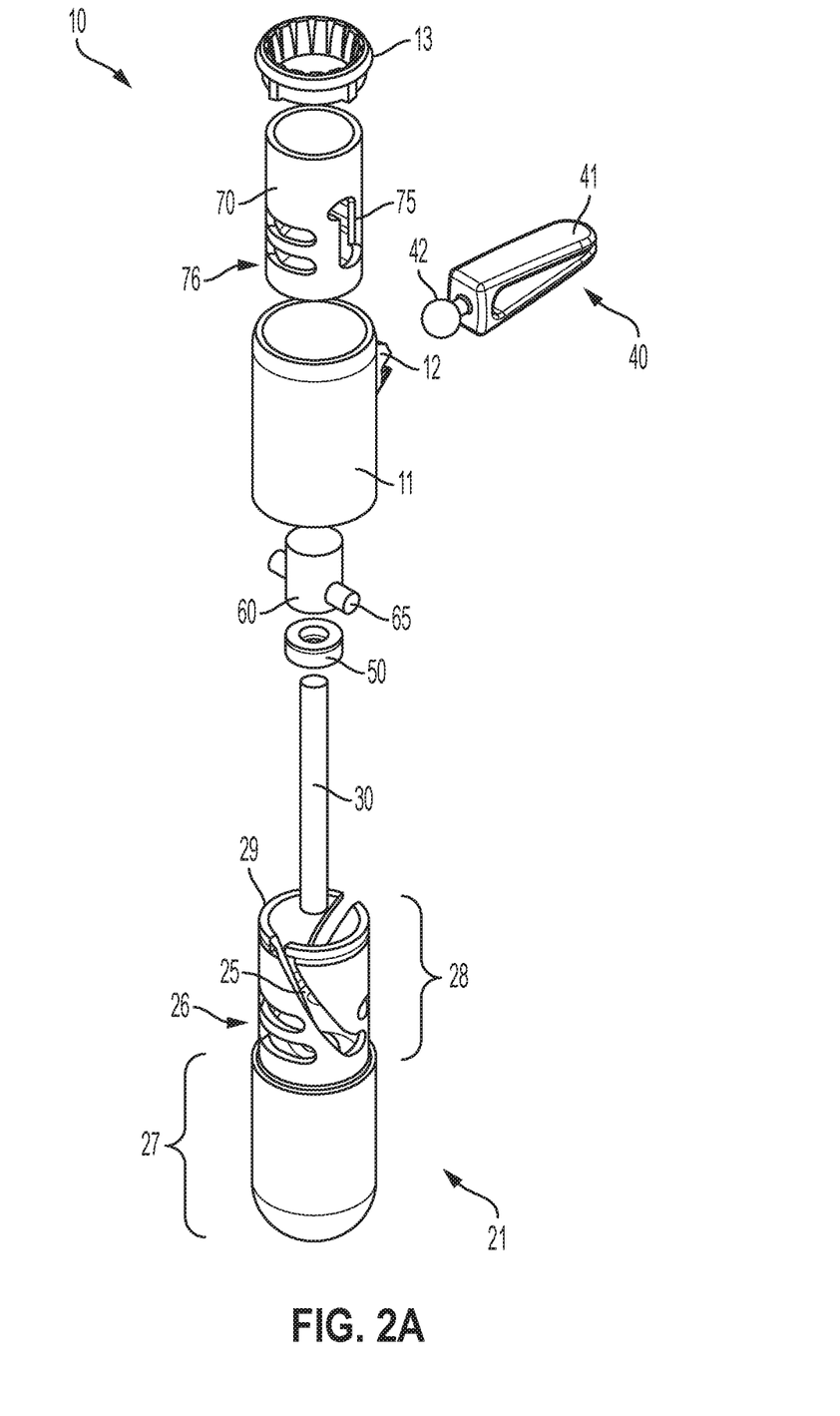
FIGS. 2A-2B are exploded views of a diffuser according to one embodiment.
Figure 2B:
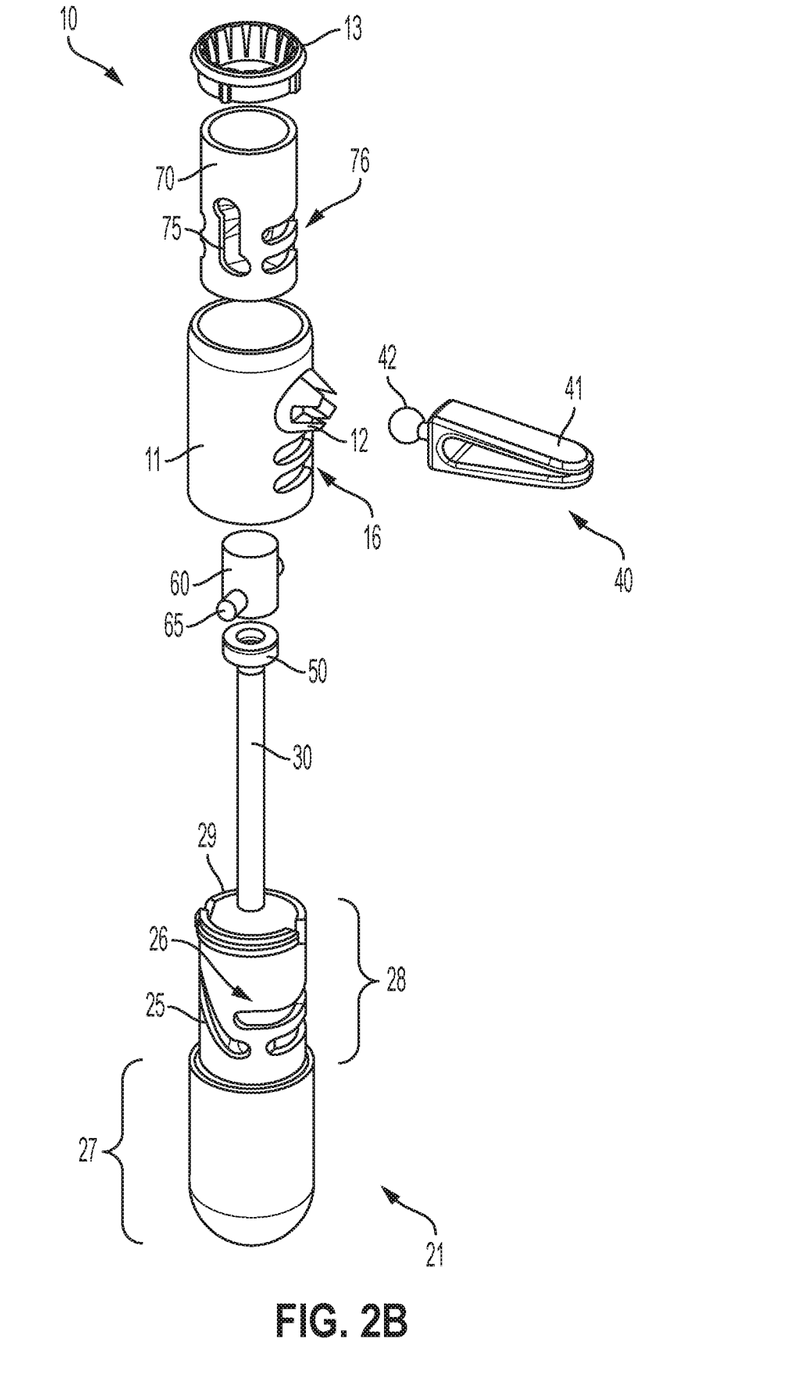

FIGS. 2A-2B are exploded views of the diffuser 10 shown in FIG. 1. As shown therein, the diffuser 10 defines an outer diffuser body comprising a first body 11 (e.g., an upper body) and a second body 21 (e.g., a lower body). In certain embodiments, the first body 11 and the second body 21 may comprise an identical material to provide the diffuser 10 with a uniform appearance. However, in the embodiments shown in FIGS. 1-2B, the first body 11 and the second body 21 may comprise different materials. For example, the first body 11 may comprise an opaque plastic material (e.g., polyvinyl chloride) and the second body 21 may comprise a transparent or translucent material (e.g., PET). Because the second body 21 defines a reservoir portion 27 having an interior cavity therein, the transparent or translucent configuration enables a user to monitor an amount of volatile substance composition 100 remaining within the diffuser 10. As shown FIGS. 1-2B, the first body 11 is hollow, defining an interior volume surrounded by an interior surface of the hollow first body 11. The second body 21 defines a fitting portion 28 configured to fit within the hollow first body 11, and a reservoir portion. The fitting portion 28 may define a fitting ring 29 (e.g., along a top-most edge of the fitting portion of the second body 21) configured to interference fit within a groove defined within the interior surface of the hollow first body 11 (or to interference fit with a portion of a diffuser portion 13 discussed herein). When the first body 11 is secured relative to the second body 21, an exterior surface of the first body 11 may be at least substantially aligned with an exterior surface of the reservoir portion 27 of the second body 21 to provide a pleasing, smooth aesthetic of the diffuser 10.

Moreover, as shown in FIGS. 1-2B, the hollow first body 11 defines an air exhaust 14, such as the top opening of the hollow first body 11 (opposite the lower opening configured for accepting the fitting portion 28 of the second body 21 therein). The air exhaust 14 may be surrounded by a diffuser portion 13 providing a pleasing aesthetic to the top of the diffuser 10. The diffuser portion 13 may be integrally formed with the first body 11 or, as shown in the figures, the diffuser portion 13 may be embodied as a separate component that may be secured relative to the first body 11. The diffuser portion 13 may be friction fit with the interior surface of the hollow first body 11 (or the exterior surface of the first body 11), or the diffuser portion may be rotatably interference fit with the fitting portion 28 of the second body 21, thereby entrapping the hollow first body 11 between the diffuser portion 13 and the second body 21. It should be understood that the diffuser portion 13 may be secured relative to the first body 11 via any of a variety of other attachment mechanisms (e.g., adhesive, fasteners, interference fitting with the first body 11, and/or the like).

In the illustrated embodiment, the diffuser body (comprising the first body 11 and the second body 21) may have an at least substantially circular cross-section, such that the second body 21 remains aligned relative to the first body 11 when rotating the second body 21 relative to the first body 11 as discussed in detail herein. However, it should be understood that any cross-sectional shape may be utilized for the diffuser body, depending on a desired aesthetic of the diffuser body.

Figure 5A:
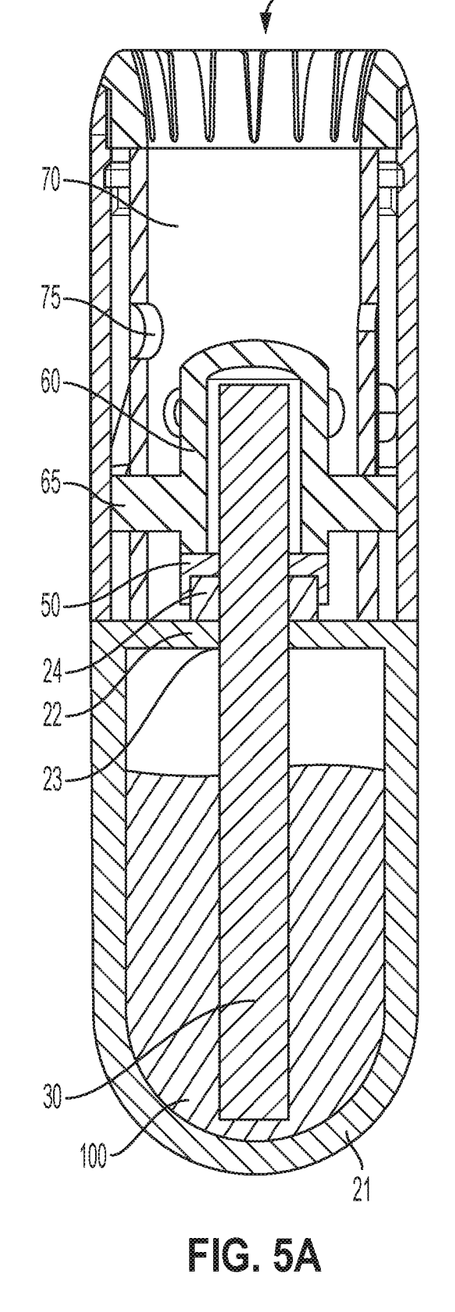
FIGS. 5A-5B are cutaway side views of a diffuser in a sealed configuration and an exposed configuration, respectively, according to one embodiment.
Figure 5B:
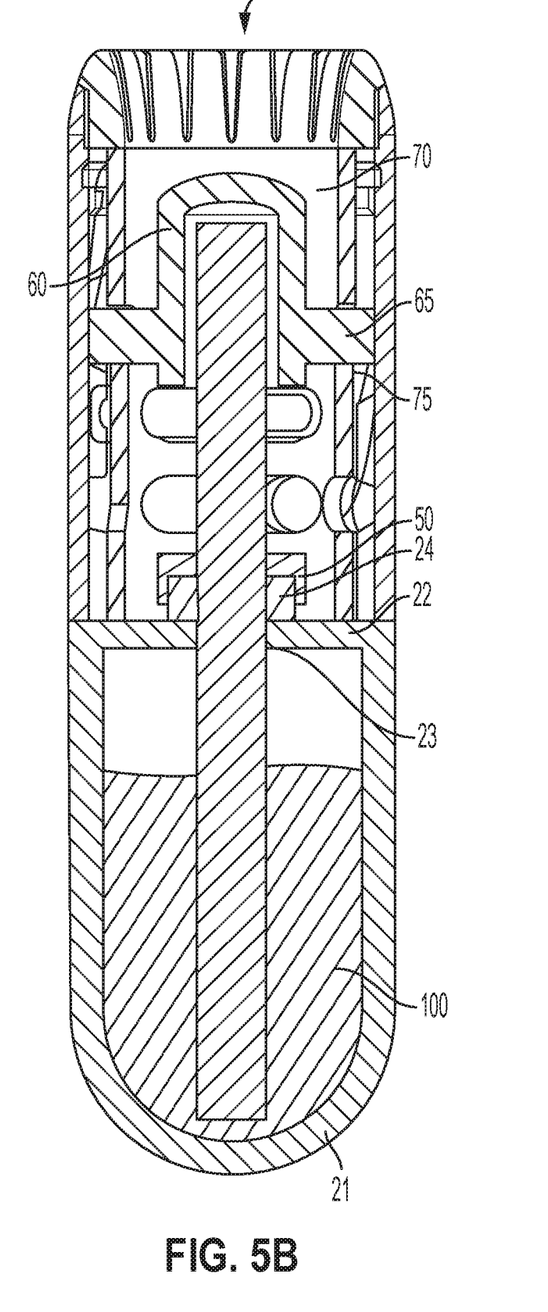

As shown most clearly in the exploded views of FIGS. 2A-2B and in the side cutaway views of FIGS. 5A-5B, the second body 21 of the illustrated embodiments is an integrally formed component. However, it should be understood that in various embodiments the second body 21 may comprise a plurality of separate components secured relative to one another to form the described configuration.

The second body 21 of the illustrated embodiment defines a hollow reservoir portion 27 configured for maintaining a volatile substance composition 100 therein. The hollow reservoir portion 27 may be defined within sidewalls of the second body 21 (which may converge to form a bottom wall of the hollow reservoir portion 27) and a reservoir upper wall 22. The reservoir upper wall 22 may be defined at approximately a mid-point of the height of the second body 21 (as shown in FIGS. 5A-5B), although the reservoir upper wall 22 may be positioned at other locations of the second body 21, depending on a desired configuration of the diffuser 10. In the illustrated embodiment, the reservoir upper wall 22 defines a wick aperture 23 extending therethrough. In the illustrated embodiment, the wick aperture 23 is aligned with a central axis of the second body 21, such that rotationally movable components of the diffuser 10 (discussed herein) rotate about a central axis of the wick aperture 23, and wick 30, which extends through the wick aperture 23 and is at least substantially concentrically located with the wick aperture 23. The wick aperture 23 may have a cross-sectional size configured to have a tight, frictional fit with the exterior surface of the wick 30, and accordingly the wick aperture 23 may have a shape corresponding to the cross-sectional shape of the wick 30. For example, for a round wick 30, the wick aperture 23 has a round shape having a size corresponding to the size of the wick 30.

Moreover, as shown in FIGS. 5A-5B, the wick aperture 23 may be surrounded by a gasket seat 24 on an upper surface of the reservoir upper wall 22 (opposite the reservoir). The gasket seat 24 is defined by a raised portion surrounding the wick aperture 23 that may be engaged by a gasket 50 associated with a wick cap 60 to seal the wick 30 and wick aperture 23 to prevent volatile substance composition 100 from leaking from the reservoir, as discussed herein. As discussed herein, the gasket 50 may have a lower opening configured to surround at least a portion of the exterior surface of the gasket seat 26, and an interior surface of the lower opening may be configured to engage a top surface of the gasket seat 26.

The reservoir upper wall 22 of the illustrated embodiment is surrounded by the fitting portion 28 of the second body 21, which defines a hollow tubular shape extending away from a top surface of the reservoir upper wall 22. As alluded above, the exterior surface of the fitting portion 28 may have a smaller diameter than the reservoir portion 27, such that the fitting portion 28 may fit within an interior volume of the first body 11, while the reservoir portion 27 may be aligned with an exterior surface of the first body 11.

The wick 30 comprises a porous material, such as a paper material, a wood material, and/or the like. A lower end of the wick 30 is positioned proximate a lower end of the reservoir (defined within the hollow interior of the second body 21), and is therefore submerged within the liquid volatile substance composition 100 within the reservoir portion 27. The wick 30 extends upwards, away from the lower end of the wick 30, through the wick aperture 23 to a selectably exposed upper portion positioned above the reservoir upper wall 22. The wick 30 is thus configured to move liquid volatile substance composition 100 up the length of the wick 30 (e.g., via capillary action), from the interior of the reservoir portion 27 to the selectably exposed upper portion positioned above the reservoir upper wall 22. When the diffuser 10 is in the exposed configuration (as shown in the cutaway view of FIG. 5B), fragrance composition 100 existing within the exposed wick portion 30a evaporates from the wick 30 and mixes with air flowing through the interior of the diffuser 10, and exits the diffuser 10 through the air exhaust 14. When the diffuser 10 is in the sealed configuration however, the portion of the wick 30 positioned above the reservoir upper wall 22 is enclosed within the wick cap 60, thereby preventing air flowing through the diffuser 10 from interacting with the surface of the wick 30, and impeding evaporation of the volatile substance composition 100 from the wick 30 into the surrounding air.

As further discussed in detail herein, the second body 21 is rotatable relative to the first body 11, which causes the wick cap 60 and gasket 50 to move along a central axis of the diffuser 10 and wick 30 to selectively seal the wick aperture 23 and wick 30 to prevent volatile substance composition 100 from leaking from the interior of the reservoir portion 27. Thus, the fitting portion 28 of the second body 21 defines a splined cam slot 25 (spiraling at least partially around a perimeter of the fitting portion 28 of the second body 21) configured to engage a cam pin 65 (collectively the cam slot 25 and cam pin 65 define portions of a cam mechanism) of the wick cap 60 to translate the rotational movement of the second body 21 into linear movement of the wick cap 60 along the central axis of the diffuser 10 and wick 30. In certain embodiments, the cam slot 25 is undersized relative to the diameter of the cam pin 65, such that the cam pin 65 frictionally engages edges of the cam slot 25 to maintain a desired position of the cam pin 65 along the length of the cam slot 25 (and to accordingly maintain a desired location of the wick cap 60 within the diffuser 10, and by extension, a desired length of exposed wick 30a, which impacts the intensity of volatile substance released by the diffuser 10). Accordingly, the location of the cam pin 65 within the cam slot 25 (and consequently within the travel slot 75) is infinitely adjustable between a lower-most position corresponding to the sealed configuration of the diffuser 10 and an upper-most position corresponding to the most-exposed configuration of the diffuser 10.

Moreover, the fitting portion 28 of the second body 21 defines one or more second body vents 26 that may be selectively aligned with others of the air intake vents 6 (first body vents 16 and/or interior body vents 76) to adjust the amount of air flow enabled to flow into the interior of the diffuser 10 by adjusting the effective size of the air intake vents 6. Rotation of the second body 21 relative to the first body 11 repositions the second body vents 26 relative to the first body vents 16 and/or interior body vents 76, thereby changing the effective size of the air intake vents 6 of the diffuser 10. In the illustrated embodiment, the positioning of the second body vents 26 may be configured to compliment the positioning of the wick cap 60 to further adjust the intensity of volatile substance released from the diffuser 10. For example, rotating the second body 21 to lower the wick cap 60 (thereby decreasing the length of the exposed wick portion 30a may also decrease the effective size of the air intake vents 6 to decrease the intensity of volatile substance released from the diffuser 10. Likewise, rotating the second body 21 to raise the wick cap 60 (thereby increasing the length of the exposed wick portion 30*a* may also increase the effective size of the air intake vents 6 to increase the intensity of volatile substance released from the diffuser 10.

Certain embodiments of the diffuser 10 are configured to be secured adjacent and/or relative to a support device, such as an air vent of an automotive air circulation system to circulate volatile substance throughout an automotive interior. The diffuser 10 may thus be secured relative to the automotive air vent, such that air exhausted from the automotive air vent may cause volatile substance composition 100 from the diffuser 10 to be circulated throughout the automotive interior. Accordingly, the diffuser 10 additionally comprises a mounting mechanism, such as the vent clip 40 shown in the figures, which is configured to detachably engage a vent slat of an automotive air vent (not shown) to secure the diffuser 10 relative to the automotive air vent. However, it should be understood that other mounting mechanism configurations may be utilized, such as an adhesive-based mounting mechanism, a fastener-based mounting mechanism (e.g., screws, nails, and/or the like), a magnet-based mounting mechanism, a hook-and-loop mounting mechanism, and/or the like. In certain embodiments, the mounting mechanism (such as the vent clip 40) may be configured to self-level or self-right the diffuser 10 to avoid spilling of a volatile substance composition 100. For example, if a user turns the diffuser 10 sideways when installing the mounting mechanism relative to a support device, the diffuser 10 may self-pivot to an upright configuration as shown in the figures (e.g., with the reservoir portion 27 located below a wick 30).

The illustrated vent clip 40 comprises a resilient material (e.g., a semi-rigid plastic material, such as PVC) configured such that securing arms 41 may deform away from one another while a vent slat is inserted therebetween, and the securing arms 41 thereafter rebound toward one another to entrap the vent slat therebetween to secure the diffuser 10 relative to the air vent.

The securing arms 41 of the vent clip 40 extend away from a base end of the vent clip 40 to a distal end of the vent clip 40. As shown, the vent clip 40 comprises two securing arms 41 defining a space therebetween adjacent the base end of the vent clip 40, and being in contact with one another at the distal end of the vent clip 40 (or being spaced at a smaller distance away from one another at the distal end of the vent clip 40 as compared with the base end of the vent clip 40).

In certain embodiments, the vent clip 40 embodies self-righting configuration by being secured relative to the diffuser 10 via a low friction joint located above a center of gravity of the diffuser 10, such that the diffuser 10 will rotate about the low friction joint under the influence of gravity to self-right the diffuser 10 into an upright orientation. By self-righting the diffuser 10 in the upright orientation, the self-righting configuration (e.g., low friction joint) decreases the likelihood of undesirable leakage of liquid volatile substance composition 100 from within the interior of the reservoir portion 27, through the wick aperture 23 (around the wick 30), which may occur if the diffuser 10 is inverted for an extended period of time while the diffuser 10 is in an exposed configuration.

In the illustrated embodiment, the low friction joint is embodied as a ball joint defined by a clip ball 42 extending away from the base portion of the vent clip 40 and a socket 12 defined on an exterior surface of the first body 11. In the illustrated embodiment, the socket 12 is aligned with the first body vents 16 such that air blown out of the air vent to which the vent clip 40 is secured is directed through the air intake vents 6 and into the interior of the diffuser 10, where the air mixes with evaporated volatile substance composition 100 and is directed out of the diffuser 10 through the air exhaust 14. The ball joint has sufficient degrees of freedom to engage horizontal air vent slats, vertical air vent slats, or other air vent slat configurations, while enabling the diffuser 10 to self-level to the upright configuration.

Moreover, the diffuser 10 additionally comprises a closure mechanism configured to move the wick cap 60 and associated gasket 50 relative to the wick 30 and gasket seat 24 of the reservoir upper wall 22 of the second body 21 between a sealed configuration in which the gasket 50 is seated on the gasket seat 24 to seal the wick cap 65 around the wick aperture 23 (as shown in the cutaway view of FIG. 5A), and a fully-exposed configuration in which the wick cap 60 and associated gasket 50 are spaced a maximum distance away from the gasket seat 24 and reservoir upper wall 22 to provide a maximum length of exposed wick portion 30*a* to air circulating through the air flow path through interior of the diffuser 10 (as shown in the cutaway view of FIG. 5B). In the sealed configuration, the closure mechanism isolates the wick 30 and the interior of the volatile substance composition reservoir portion 27 from an airflow path extending through the hollow interior of the first body 11. Moreover, in the sealed configuration, a lower opening of the gasket 50 surrounds at least a portion of the exterior surface of the gasket seat 26, and an interior surface of the lower opening sealingly engages a top surface of the gasket seat 26 to form a liquid tight seal therebetween.

As shown in the exploded views of FIGS. 2A-2B, the closure mechanism of the illustrated embodiment comprises a third body 70 (e.g., an interior body) configured to reside within the first body 11 and the fitting portion 28 of the second body 21. The third body 70 is at least substantially immobile (rotationally and linearly) relative to the first body 11 (e.g., the third body 70 may be integrally formed with the first body 11). By extension, the second body 21 is rotationally movable relative to the third body 70 (and the first body 11). Specifically, the fitting portion 28 of the second body 21 is rotatable within an annular gap defined between an exterior surface of the third body 70 and an interior surface of the first body 11. The third body 70 comprises a rigid material (e.g., a rigid plastic material) and defines a hollow tube having open upper and lower ends. The third body 70 defines third body vents 76 that may be aligned with the first body vents 16. As mentioned previously, the third body vents 76, the first body vents 16, and the second body vents 26 collectively define the air intake vents 6. Rotation of the second body 21 relative to the first body 11 and the third body 70 changes the effective size of the air intake vents 6 by selectively blocking or unblocking portions of the third body vents 76 and the first body vents 16. For example, the second body vents 26 may be positioned such that the third body vents 76 and the first body vents 16 are completely blocked when the diffuser 10 is in the sealed configuration (effectively closing the air intake vents 6 and blocking air from entering the interior of the diffuser 10 through the air intake vents 6), and the third body vents 76 and the first body vents 16 are entirely open when the diffuser 10 is in the most-exposed configuration (effectively opening the air intake vents 6 to their maximum size). In certain embodiments, the first body vents 16 and third body vents 76 may remain aligned regardless of the positioning of the second body vents 26.

Moreover, as shown in the figures, the third body 70 defines a travel slot 75 defining upper and lower positions for the cam pin 65 (and effectively defining the upper and lower positions for the wick cap 60 and associated gasket 50, corresponding to the sealed configuration and the fully-exposed configuration of the diffuser 10). The travel slot 75 is at least substantially vertical and linear, and may define lockout positions for receiving the cam pin 65 therein, corresponding to the sealed configuration and the fully-exposed configuration (e.g., embodied as small lateral indentions located at the lower and upper ends of the travel slot 75, respectively).

As mentioned throughout the specification, the closure mechanism additionally comprises an at least substantially hollow wick cap 60 having a closed upper end and an open lower end. The wick cap 60 comprises a rigid material (e.g., a rigid plastic material, such as PVC) and has a hollow interior configured to accept an upper end of the wick 30 therein. In the illustrated embodiment of the figures, the interior of wick cap 60 is oversized relative to the wick 30, such that movement of the wick cap 60 relative to the wick 30 is not impeded by frictional forces defined between the wick cap 60 and the wick 30. However, in other embodiments, the wick 30 may be frictionally engaged with the wick cap 60, and the wick 30 may move with the wick cap 60 between the sealed and exposed configurations. Moreover, the exterior of the wick cap 60 is undersized relative to the interior of the third body 70, to facilitate air flow around the wick cap 60 when flowing from the air intake vents 6 (located below the wick cap 60) to the air exhaust 14 located above the wick cap 60.

The wick cap 60 further defines one or more cam pins 65 extending laterally away from an exterior sidewall of the wick cap 60. These cam pins 65 are configured to interact with the travel slots 75 of the third body 70 and the cam slots 25 of the fitting portion 28 of the second body 21 to guide the wick cap 60 (and associated gasket 50) between the lower and upper positions corresponding to the sealed configuration and the fully-exposed configuration of the diffuser 10, respectively. The cam pins 65 have a length (measured perpendicular to the exterior sidewall of the wick cap 60 from which the cam pins 65 extend) sufficient to extend entirely through the travel slot 75 and at least partially through the cam slot 25. Accordingly, each cam pin 65 is configured to engage edges of the travel slot 75 and the cam slot 65 to guide the wick cap 60 linearly (vertically) between lower and upper positions. Thus, as the second body 21 is rotated, the cam slot 25 applies a force component to the cam pin 65 having both a horizontal and vertical force component. The horizontal force component presses the cam pin 65 against a side edge of the travel slot 75 (effectively preventing lateral movement of the cam pin 65, and consequently preventing rotational movement of the wick cap 60 relative to the first body 11 and third body 70). However, at the lower end of the travel slot 75 and the upper end of the travel slot 75, the horizontal force component may move the cam pin 65 laterally a short distance (thereby enabling the wick cap 60 to rotate a small angular distance) into or out of lockout positions extending laterally away from the vertical travel slot 75.

Figure 3:
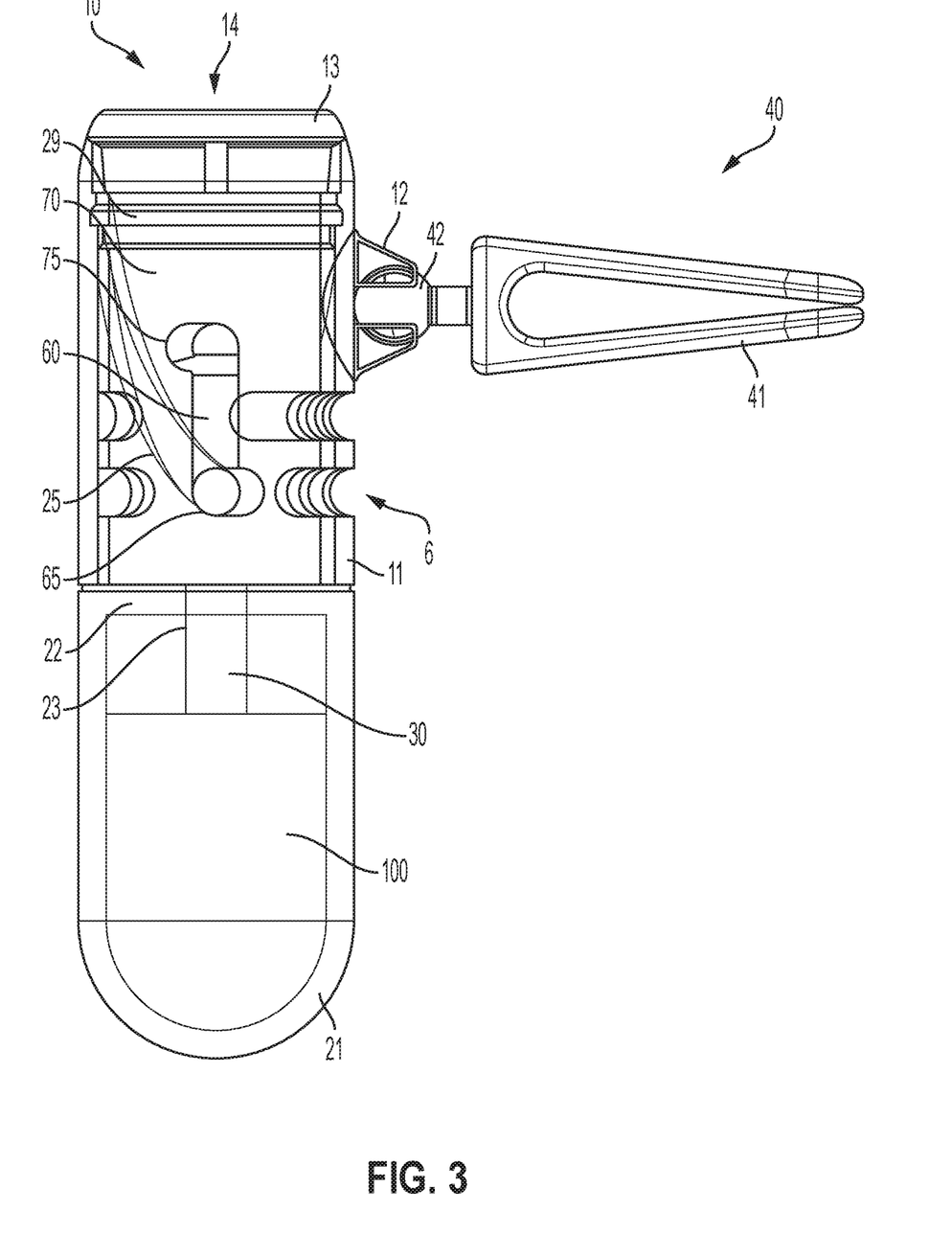
FIGS. 3-4 are partial cutaway side views of a diffuser in a sealed configuration and an exposed configuration, respectively, according to one embodiment.
Figure 4:
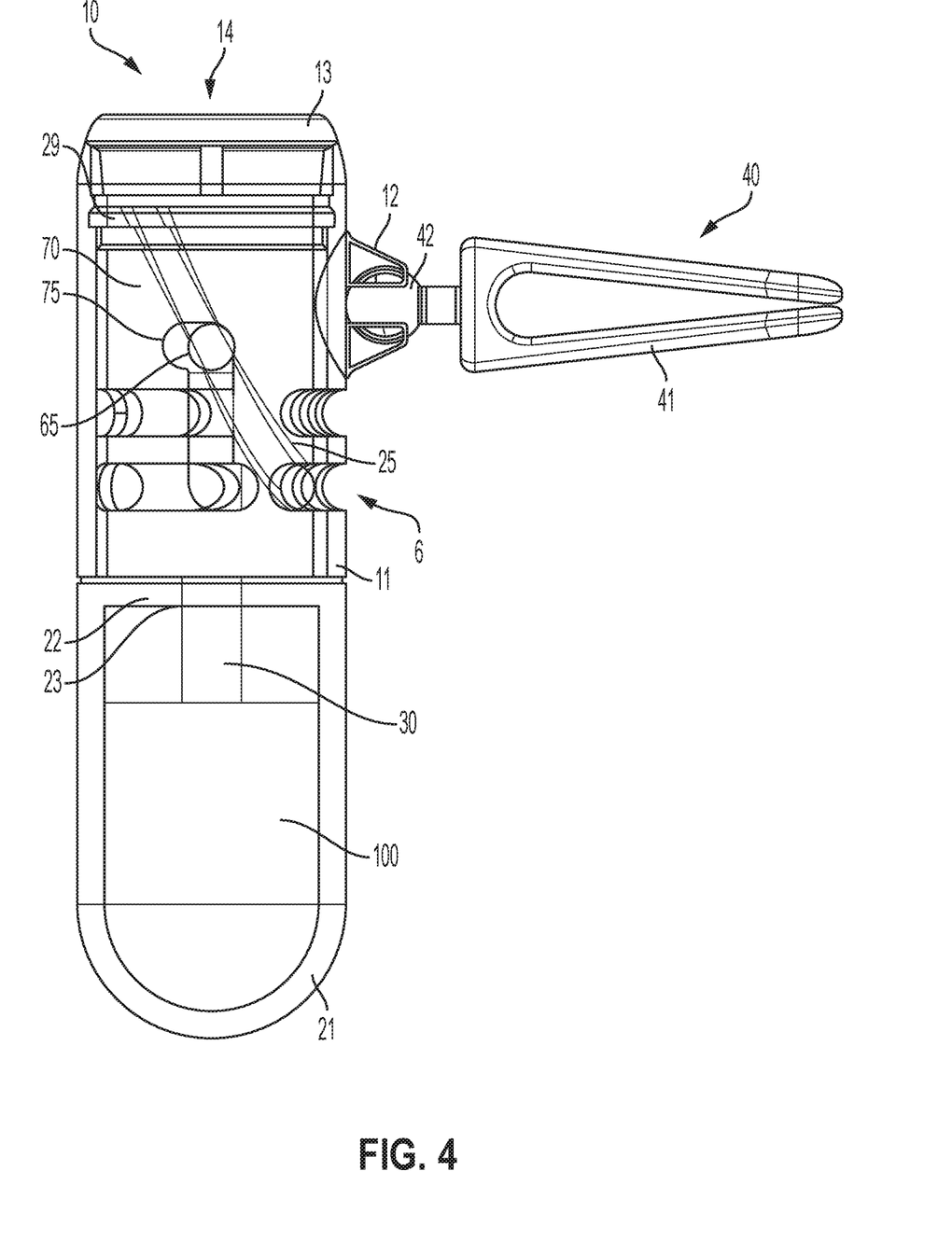

The vertical force component applied to the cam pin 65 by the cam slot 25 of the rotating second body 21 causes the cam pin 65 to move vertically within the travel slot 75 between a lower end of the travel slot 75 and an upper end of the travel slot 75. FIGS. 3-4 illustrate side views of the diffuser 10 with the first body 11 and second body 21 illustrated with transparency to demonstrate the positioning of the cam slot 25 and the cam pin 65 relative to the travel slot 75 as the second body 21 is rotated. As shown therein, as the second body 21 is rotated, the cam slot 25 rotates relative to the cam pin 65, which is laterally entrapped within the travel slot 75. When moving from the configuration of FIG. 3 (which corresponds to the sealed configuration also shown in cutaway in FIG. 5A) to the configuration of FIG. 4 (which corresponds to the fully-exposed configuration also shown in cutaway in FIG. 5B), the cam slot 25 is rotated from a first position in which a lower end of the cam slot 25 is aligned with the travel slot 75 to a second position in which an upper portion of the cam slot 25 is aligned with the travel slot 75, thereby moving the cam pin 65 (and the wick cap 60) vertically upwards.

Finally, as mentioned throughout this description, the closure mechanism further comprises a gasket 50 comprising a flexible material (e.g., a flexible rubber material, flexible plastic material, and/or the like) configured to form a liquid-tight seal between a bottom edge of the wick cap 60 and the gasket seat 24 of the reservoir upper wall 22 when depressed between the wick cap 60 and the gasket seat 24 in the sealed configuration of the diffuser 10. In certain embodiments, the gasket 50 may remain immovably seated on the gasket seat 24, such that the wick cap 60 moves relative to the gasket 60. In such configurations, the lower edge of the wick cap 60 contacts and sealingly engages an upper surface of the gasket 60 when the diffuser 10 is in the sealed configuration. In such embodiments, the upper surface of the gasket 60 has a shape corresponding to the lower edge of the wick cap 60. In the illustrated embodiment, for example, the lower edge of the wick cap 60 is at least substantially planar, and accordingly the upper surface of the gasket 50 is similarly at least substantially planar.

In other embodiments, the gasket 50 may be secured relative to the lower edge of the wick cap 60, such that the gasket 50 moves with the associated wick cap 60 relative to the gasket seat 24. In such configurations, the lower edge of the gasket 50 contacts and sealingly engages an upper surface (and side edge surfaces in certain embodiments) of the gasket seat 24 when the diffuser is in the sealed configuration.

Figure 6:
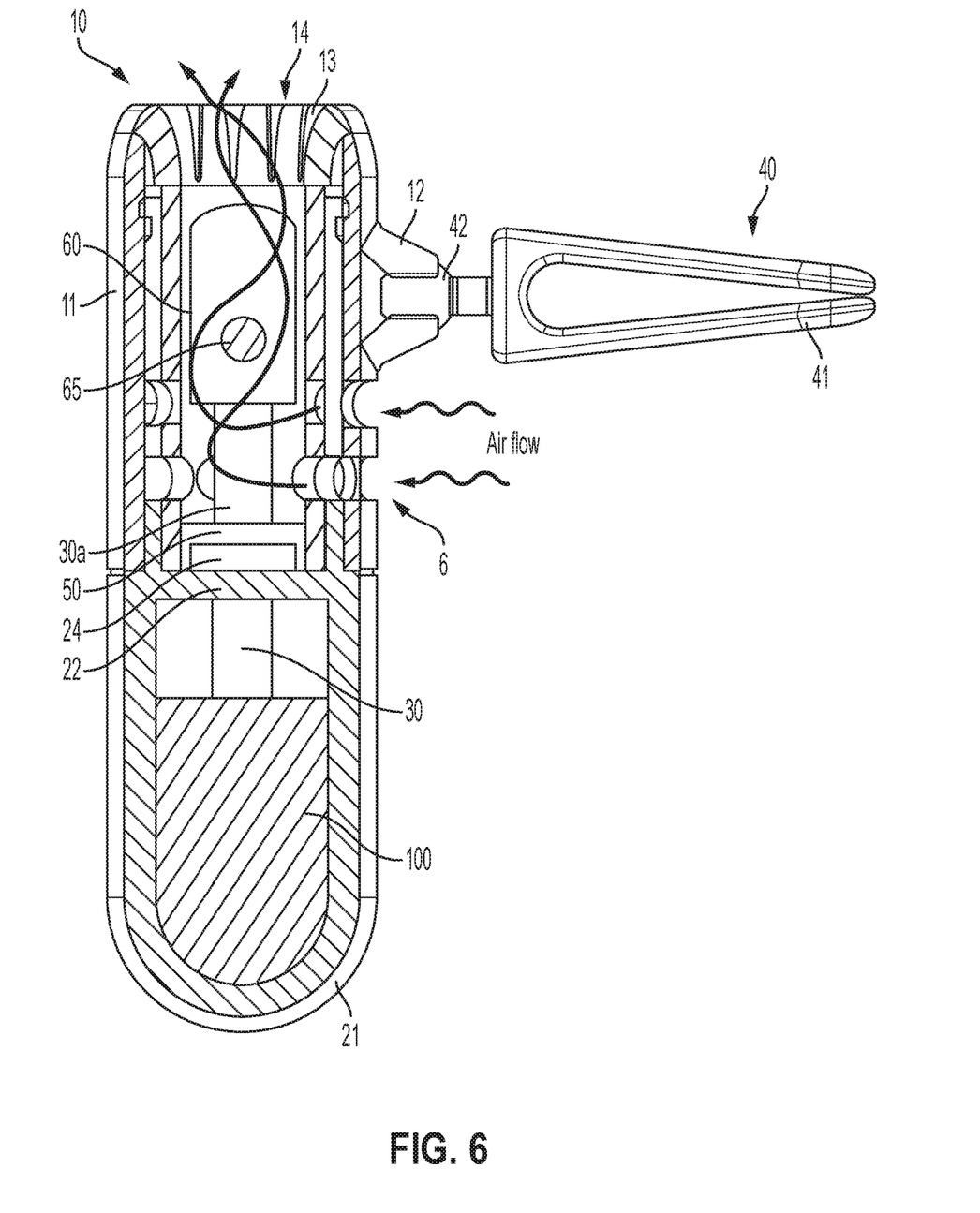
FIG. 6 is a partial cutaway side view of a diffuser illustrating an air flow path therethrough according to one embodiment.

FIG. 6 depicts an air flow path through the diffuser 10 according to one embodiment. As shown therein, air enters through the air intake vents 6 extending through a side of the diffuser 10 (extending through the first body vents 16, second body vents 26, and third body vents 76. The air circulates around the exposed wick portion 30a to mix with evaporated volatile substance composition 100 before flowing around an exterior surface of the wick cap 60 (and around cam pins 65) before flowing out of the air exhaust 14, which is located through a top of the diffuser 10 in the illustrated embodiment. However, it should be understood that the air intake vents 6 and air exhaust 14 may be located at alternative locations of the diffuser 10.

In use, the diffuser 10 may be opened to a desired level of exposure—selected between the sealed configuration and the fully-exposed configuration, to provide a desired level of volatile substance (e.g., fragrance) diffusion.

A user may secure the diffuser 10 in a desired location via the included mounting mechanism (e.g., vent clip 40), such as relative to a vent slat of an automotive interior air circulation system. Once secure, the user may allow the diffuser 10 to rotate under the influence of gravity, about a pivot point of the mounting mechanism, to align the diffuser 10 in an upright orientation.

A user may select the desired level of exposure of the diffuser 10 by rotating the second body portion 21 relative to the first body portion 11. The user may select the desired level of exposure either before securing the diffuser 10 in the desired location, or after securing the diffuser 10 in the desired location.

When the diffuser 10 is provided in the sealed configuration (which prevents unintentional spillage of liquid volatile composition 100 from the reservoir), the wick cap 60 may be provided in a lockout position, in which the cam pin(s) 65 of the wick cap 60 are interference fit within lockout portions of the travel slots 75 and/or cam slots 25. Thus, rotating the second body portion 21 relative to the first body portion 11 (in a first direction) first causes the cam pin(s) 65 to disengage the lockout portions of the travel slots 75 and/or cam slots 25 (e.g., via lateral movement of the cam pin(s) 65 relative to the travel slots 75 and/or cam slots 25) and then causes the cam pin(s) 65 to move upwards within the travel slots 75 due to vertical forces imparted on the cam pin(s) 65 by edges of the splined cam slots 25 as the second body portion 21 rotates. This causes the wick cap 60 to move upward, away from the reservoir upper wall 22, thereby exposing a portion of the wick 30 to the air flow path extending through the diffuser body.

The cam pin(s) 65 remain frictionally engaged with side edges of the splined cam slots 25 after disengaging the lockout portions of the travel slots 75 and/or cam slots 25, thereby maintaining a selected position of the cam pin(s) 65 relative to the splined cam slots 25 and maintaining a desired level of exposure of the diffuser 10 selected by the user.

To reseal the diffuser 10, the user rotates the second body portion 21 relative to the first body portion 11 in an opposite direction (in a second direction). The edges of the splined cam slots 25 impart vertical downward forces on the cam pin(s) 65, which causes the cam pin(s) 65 (and the wick cap 60) to move downwards until the wick cap 60 compresses the gasket 50 between the wick cap 60 and the gasket seat 24 to isolate the wick 30 and reservoir from the air flow path extending through the first body 11. Continuing to rotate the second body portion 21 relative to the first body portion 11 causes the cam pin(s) 65 to rotate past interference fit protrusions of the travel slots 75 and/or cam slots 25 and into the lockout portions of the travel slots 75 and/or cam slots 25.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, although not shown in the figures, various embodiments of the diffuser 10 may define an indicator feature to indicate to a user whether the diffuser 10 is in the sealed or exposed configurations. The indicator may be a binary indicator—indicating simply whether the diffuser 10 is in the sealed configuration or not (regardless of the selected degree of exposure selected by the user). Alternatively, the indicator may be a continuous indicator that may provide an indicator to a user of the degree of exposure of the diffuser 10 (between the sealed configuration and a fully-exposed configuration). The indicator may be defined as a slot within a first body 11 and one or more indicators on an exterior surface of the fitting portion 28 of the second body 21 that may be selectively aligned with the slot based on the rotational position of the second body 21 relative to the first body 11 (which corresponds to the vertical position of the wick cap 60 and associated gasket 50, and consequently the degree of exposure of the diffuser 10). However, it should be understood that any of a variety of other indicator configurations may be utilized. For example, the indicator may be defined by one or more markers indicated on an exterior surface of the second body 21 and corresponding markers indicated on an exterior surface of the first body 11. These markers may be positioned such that the markers are aligned when the diffuser 10 is in the sealed configuration.

Moreover, as noted briefly above, one or more solid polymers embodied as volatile composition carriers (e.g., polymers having volatile compositions mixed throughout) may form at least a portion of a diffuser 10 body (e.g., a portion of a first body 11) or may be secured to an exterior surface of a diffuser body 10 (e.g., secured to a portion of the first body 11). As a specific example, a fragrant polymer may be secured to an exterior surface of a diffuser 10 embodied as a fragrance diffuser, to provide a multi-scent configuration of the diffuser 10.

Other multi-scent configurations of diffusers 10 may be implemented as well. As yet another example, a diffuser 10 may comprise a plurality of reservoirs (e.g., defined within a single second body 21 and separated by a solid divider wall therein) each with an associated wick 30 extending therefrom. Portions of these wicks 30 extending from the respective reservoirs may be positioned and configured such that a single wick cap 60 (which may have a segmented interior corresponding to each wick 30 or may have a single interior portion configured to selective enclose all of the wicks 30 therein) may selectively enclose all of the wicks simultaneously when the diffuser 10 is in the sealed configuration. Alternatively, a plurality of wick caps 60 may be independently movable (e.g., by rotating different portions of a diffuser body 10) between respective sealed configurations and fully-exposed configurations, thereby enabling a user to independently adjust the intensity of each fragrance diffused therefrom.

That which is claimed:
1. A diffuser comprising:
a first body portion defining a hollow interior and having an air flow path extending therethrough;
a second body portion secured to the first body portion and rotatable relative to the first body portion, the second body portion defining a reservoir for storing a volatile substance composition;
a third body portion positioned within the hollow interior of the first body portion and rotationally immobile relative to the first body portion, the third body portion comprising a sidewall;
a wick configured for holding the volatile substance composition therein and positioned at least partially within the hollow interior of the first body portion; and
a closure mechanism comprising a wick cap having an exterior surface, a cam slot defined within the second body portion, and a vertical travel slot extending through the sidewall of the third body portion, the wick cap comprising a cam pin extending away from the exterior surface of the wick cap and into the vertical travel slot and the cam slot, wherein the wick cap is positioned within the hollow interior of the first body portion and movable relative to the first body portion to selectably isolate the wick from the air flow path extending through the first body portion.

2. The diffuser of claim 1, wherein:
the wick extends from the reservoir and into the hollow interior of the first body portion; and
the wick cap is movable relative to the first body portion to selectably isolate the wick and the reservoir from the air flow path extending through the first body portion.

3. The diffuser of claim 2, wherein the wick cap is movable linearly relative to the first body portion between:
a sealed configuration in which the wick and the volatile substance composition are isolated from the air flow path; and
an exposed configuration in which at least a portion of the wick positioned within the hollow interior of the first body portion is exposed to the air flow path.

4. The diffuser of claim 3, wherein the reservoir defines a wick aperture extending therethrough and the wick aperture is surrounded by a gasket seat, and
wherein, in the sealed configuration, the wick cap depresses a gasket against the gasket seat.

5. The diffuser of claim 3, wherein the closure mechanism is configured to convert rotational movement of the second body portion relative to the first body portion into linear movement of the wick cap between the sealed configuration and the exposed configuration.

6. The diffuser of claim 3, wherein the closure mechanism defines one or more lockout positions to selectably lock the cam pin in:
a first vertical position corresponding to the sealed configuration; or
a second vertical position corresponding to the exposed configuration.

7. The diffuser of claim 2, wherein the wick cap is movable relative to the first body portion to selectably isolate the wick and the reservoir from the air flow path extending through the first body portion based on a rotational position of the second body portion relative to the first body portion.

8. The diffuser of claim 1, further comprising a clip for securing the diffuser relative to a support device, wherein the clip is secured to the first body portion by a ball joint at a location above a center of gravity of the diffuser.

9. The diffuser of claim 1, wherein the third body portion is integrally formed with the first body portion.

10. The diffuser of claim 1, wherein an annular gap is defined between an exterior surface of the third body portion and an interior surface of the first body portion, the second body being rotatable relative to the first body portion within the annular gap.

11. A diffuser comprising:
a body defining a hollow interior and having an air flow path extending therethrough;
a wick configured for holding a volatile substance composition therein and positioned at least partially within the hollow interior of the body;
a closure mechanism configured to selectably isolate the wick from the air flow path extending through the body, wherein the closure mechanism comprises a wick cap movable linearly between:
a sealed configuration in which the wick and the volatile substance composition are isolated from the air flow path; and
an exposed configuration in which at least a portion of the wick positioned within the hollow interior of the body is exposed to the air flow path; and
a reservoir, wherein the wick extends from the reservoir and into the hollow interior of the body and the closure mechanism is configured to selectably isolate the wick and the reservoir from the air flow path extending through the body, wherein the reservoir defines a wick aperture extending therethrough and the wick aperture is surrounded by a gasket seat, and wherein, in the sealed configuration, the wick cap depresses a gasket against the gasket seat, wherein the body is a first body portion, the reservoir is defined within a second body portion rotationally secured relative to the first body portion, a third body portion is positioned within the hollow interior of the first body portion and rotationally immobile relative to the first body portion, and the closure mechanism additionally comprises a cam mechanism configured to convert rotational movement of the second body portion relative to the first body portion into linear movement of the wick cap between the sealed configuration and the exposed configuration, wherein the cam mechanism is defined by:
one or more splined cam slots within a sidewall of the second body portion;
a vertical travel slot extending through a sidewall of the third body portion; and
one or more cam pins each extending laterally away from an exterior surface of the wick cap and into the vertical travel slot and one of the one or more splined cam slots.

12. The diffuser of claim 11, wherein the cam mechanism defines one or more lockout positions to selectably lock the cam pin in:
a first vertical position corresponding to the sealed configuration; or
a second vertical position corresponding to the exposed configuration.

13. The diffuser of claim 11, wherein the closure mechanism is configured to selectably isolate the wick and the reservoir from the air flow path extending through the first body portion based on the rotational position of the second body portion relative to the first body portion.

14. The diffuser of claim 11, further comprising a clip for securing the diffuser relative to a support device, wherein the clip is secured to the first body portion by a ball joint at a location above a center of gravity of the diffuser.

15. A method of assembling a diffuser, the method comprising:
providing a first body portion, the first body portion defining a hollow interior and having an air flow path extending therethrough;
securing a second body portion to the first body portion, the second body portion being rotatable relative to the first body portion and defining a reservoir for storing a volatile substance composition;
providing a third body portion within the hollow interior of the first body portion, the third body portion including a sidewall and being rotationally immobile relative to the first body portion;
positioning a wick at least partially within the hollow interior of the first body portion, the wick configured for holding the volatile substance composition therein; and
providing a wick cap of a closure mechanism in the hollow interior of the first body portion and on the wick, the closure mechanism further including a cam slot defined within the second body portion and a vertical travel slot extending through the sidewall of the third body portion, the wick cap having an exterior surface and a cam pin extending away from the exterior surface of the wick cap and into the vertical travel slot and the cam slot, wherein the wick cap is movable relative to the first body portion to selectably isolate the wick from the air flow path extending through the first body portion.

16. The method of claim 15, wherein the wick extends from the reservoir and into the hollow interior of the first body portion, and wherein the wick cap is movable relative to the first body portion to selectably isolate the wick and the reservoir from the air flow path extending through the first body portion.

17. The method of claim 16, wherein the wick cap is movable linearly relative to the first body portion between:
 a sealed configuration in which the wick and the volatile substance composition are isolated from the air flow path; and
 an exposed configuration in which at least a portion of the wick positioned within the hollow interior of the first body portion is exposed to the air flow path.

18. The method of claim 17, wherein the reservoir defines a wick aperture extending therethrough and the wick aperture is surrounded by a gasket seat, and
 wherein, in the sealed configuration, the wick cap depresses a gasket against the gasket seat.

19. The method of claim 17, wherein the closure mechanism is configured to convert rotational movement of the second body portion relative to the first body portion into linear movement of the wick cap between the sealed configuration and the exposed configuration.

* * * * *